(12) United States Patent
Berry et al.

(10) Patent No.: US 8,361,162 B2
(45) Date of Patent: Jan. 29, 2013

(54) ORTHOPAEDIC JOINT PROSTHESIS IMPLANT KIT

(75) Inventors: Daniel Berry, Rochester, MN (US); Andrew Donn, Vancouver (CA); Brian Griffiths, Hants (GB); Fiona Haig, Cambridge (GB); Graham Isaac, Huddersfield (GB); Thomas Schmalzried, Rolling Hills, CA (US)

(73) Assignee: DePuy International Limited (GB)

( * ) Notice: Subject to any disclaimer, the term of this patent is extended or adjusted under 35 U.S.C. 154(b) by 698 days.

(21) Appl. No.: 12/065,580

(22) PCT Filed: Aug. 22, 2006

(86) PCT No.: PCT/GB2006/003127
§ 371 (c)(1),
(2), (4) Date: Jul. 20, 2010

(87) PCT Pub. No.: WO2007/026119
PCT Pub. Date: Mar. 8, 2007

(65) Prior Publication Data
US 2010/0298943 A1  Nov. 25, 2010

(30) Foreign Application Priority Data
Sep. 3, 2005 (GB) .................. 05179452.2

(51) Int. Cl.
*A61F 2/32* (2006.01)
*A61F 2/36* (2006.01)
*A61F 2/30* (2006.01)

(52) U.S. Cl. ............... 623/22.12; 623/23.46; 623/23.21

(58) Field of Classification Search ............... 623/22.12, 623/23.22, 23.46, 23.26–23.28, 23.21, 23.25, 623/18.11, 23.48, 23.47, 23.43; 606/92–95, 606/99, 100, 85, 86 R
See application file for complete search history.

(56) References Cited

U.S. PATENT DOCUMENTS

| | | | | | |
|---|---|---|---|---|---|
| 3,793,650 | A | * | 2/1974 | Ling et al. .................. | 623/23.46 |
| 4,623,353 | A | * | 11/1986 | Buechel et al. ............. | 623/23.21 |
| 4,661,112 | A | * | 4/1987 | Muller ........................ | 623/23.22 |

(Continued)

FOREIGN PATENT DOCUMENTS

| | | |
|---|---|---|
| DE | 19518391 A1 | 11/1996 |
| EP | 0962197 A2 | 12/1999 |

(Continued)

OTHER PUBLICATIONS

PCT Written Opinion, 8 pages.

(Continued)

*Primary Examiner* — Alvin J. Stewart

(57) ABSTRACT

This invention relates to an orthopaedic joint prosthesis implant kit (2). The implant kit comprises a stem component (4) of an orthopaedic joint prosthesis which is intended for articulation with a mating component of the joint. The stem component has a distal end (6) and a proximal end (8), and a neck part (10) at the proximal end, and is configured for fixation in a bone cavity-using bone cement material with the distal end within the cavity and the proximal end at the opening of the cavity, and with the neck part protruding from the cavity towards the mating component of the joint. The implant kit further comprises a positioning kit (18), at least one spacer (20, 22, 24) for location between the wall of the cavity and the stem component at its proximal end, and a delivery device (26).

20 Claims, 6 Drawing Sheets

U.S. PATENT DOCUMENTS

| | | | | |
|---|---|---|---|---|
| 4,698,063 | A * | 10/1987 | Link et al. | 623/23.22 |
| 4,718,909 | A * | 1/1988 | Brown | 128/898 |
| 4,753,657 | A * | 6/1988 | Lee et al. | 623/16.11 |
| 4,770,660 | A * | 9/1988 | Averill | 623/23.22 |
| 4,815,454 | A * | 3/1989 | Dozier, Jr. | 606/94 |
| 4,827,919 | A * | 5/1989 | Barbarito et al. | 606/62 |
| 4,908,036 | A * | 3/1990 | Link et al. | 623/23.22 |
| 4,938,771 | A * | 7/1990 | Vecsei et al. | 623/23.15 |
| 4,963,155 | A * | 10/1990 | Lazzeri et al. | 623/22.42 |
| 5,258,033 | A * | 11/1993 | Lawes et al. | 623/23.13 |
| 5,376,124 | A * | 12/1994 | Gustke et al. | 623/23.28 |
| 5,480,453 | A * | 1/1996 | Burke | 623/23.21 |
| 5,658,292 | A * | 8/1997 | Axelson, Jr. | 606/86 R |
| 5,755,793 | A * | 5/1998 | Smith et al. | 623/23.48 |
| 5,766,262 | A * | 6/1998 | Mikhail | 623/23.25 |
| 5,792,143 | A * | 8/1998 | Samuelson et al. | 606/102 |
| 5,885,295 | A * | 3/1999 | McDaniel et al. | 606/86 R |
| 5,997,581 | A * | 12/1999 | Khalili | 623/23.48 |
| 6,139,584 | A * | 10/2000 | Ochoa et al. | 623/23.46 |
| 6,179,877 | B1 * | 1/2001 | Burke | 623/22.12 |
| 6,245,113 | B1 * | 6/2001 | Revie et al. | 623/23.46 |
| 6,267,785 | B1 * | 7/2001 | Masini | 623/23.22 |
| 6,344,060 | B1 * | 2/2002 | Schmotzer et al. | 623/22.12 |
| 6,371,991 | B1 * | 4/2002 | Manasas et al. | 623/22.12 |
| 6,500,209 | B1 * | 12/2002 | Kolb | 623/23.48 |
| 6,652,589 | B2 * | 11/2003 | Schmotzer et al. | 623/22.12 |
| 6,669,734 | B2 * | 12/2003 | Spotorno et al. | 623/23.48 |
| 6,746,487 | B2 * | 6/2004 | Scifert et al. | 623/22.12 |
| 6,875,239 | B2 * | 4/2005 | Gerbec et al. | 623/23.15 |
| 6,887,276 | B2 * | 5/2005 | Gerbec et al. | 623/18.11 |
| 6,893,445 | B1 * | 5/2005 | Revie et al. | 606/94 |
| 6,994,731 | B2 * | 2/2006 | Howie | 623/23.35 |
| 7,229,478 | B2 * | 6/2007 | Masini | 623/19.11 |
| 7,261,741 | B2 * | 8/2007 | Weissman et al. | 623/23.22 |
| 7,291,176 | B2 * | 11/2007 | Serra et al. | 623/22.12 |
| 7,491,242 | B2 * | 2/2009 | Pichon et al. | 623/23.21 |
| 8,029,573 | B2 * | 10/2011 | Podolsky | 623/22.42 |
| 8,070,822 | B1 * | 12/2011 | Iversen | 623/22.12 |

FOREIGN PATENT DOCUMENTS

| | | |
|---|---|---|
| EP | 0985387 A1 | 3/2000 |
| EP | 1201205 A1 | 5/2002 |
| WO | WO 01/64143 A2 | 9/2001 |

OTHER PUBLICATIONS

International Search Report, dated Nov. 10, 2006, 5 pages.
UK Search Report, dated Dec. 16, 2005, 3 pages.

* cited by examiner

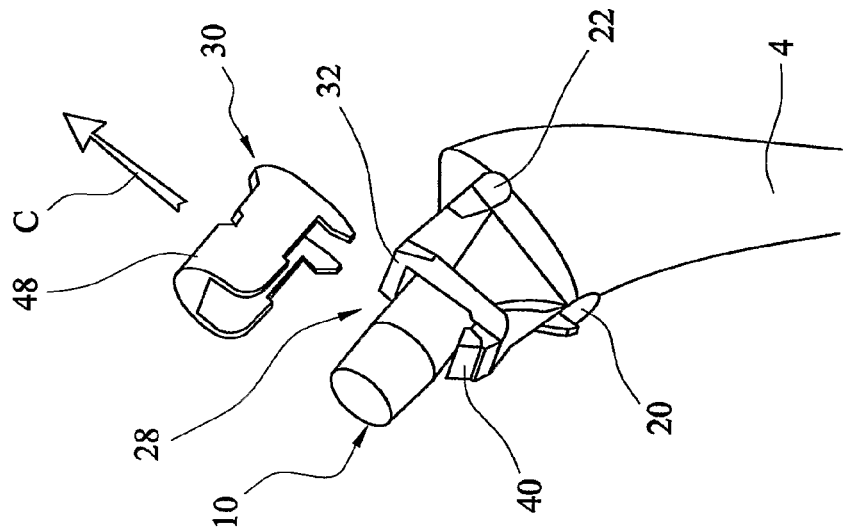
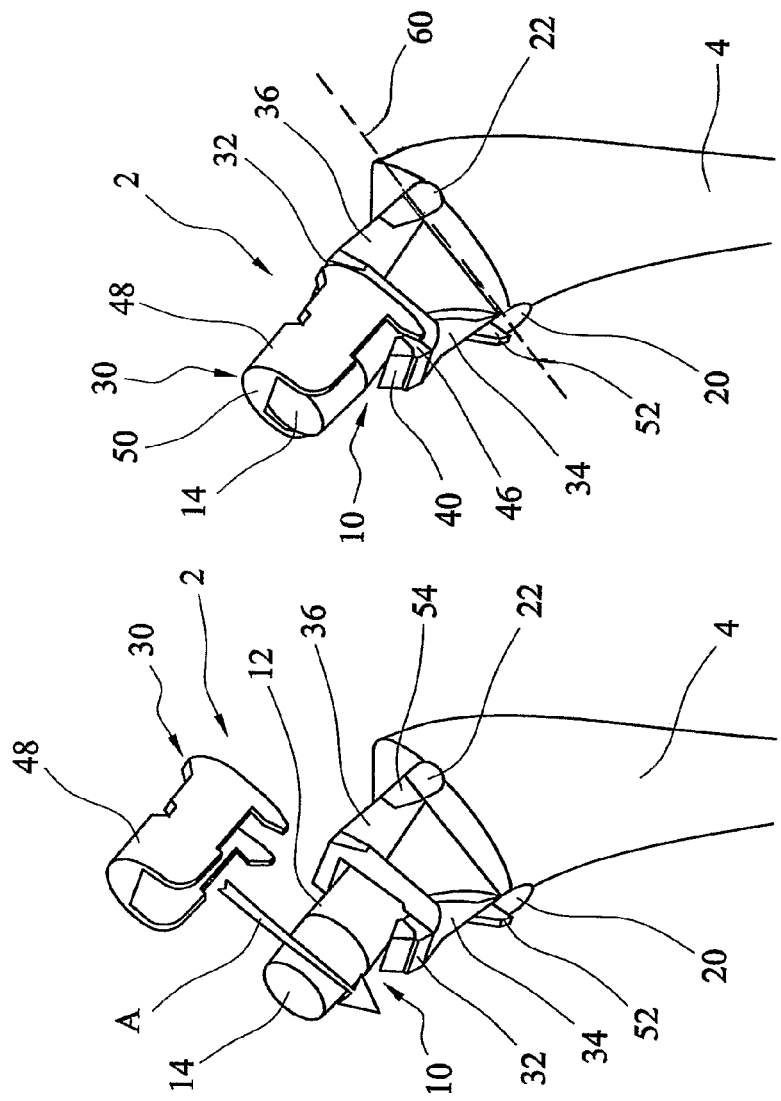
FIG. 2  FIG. 3  FIG. 4

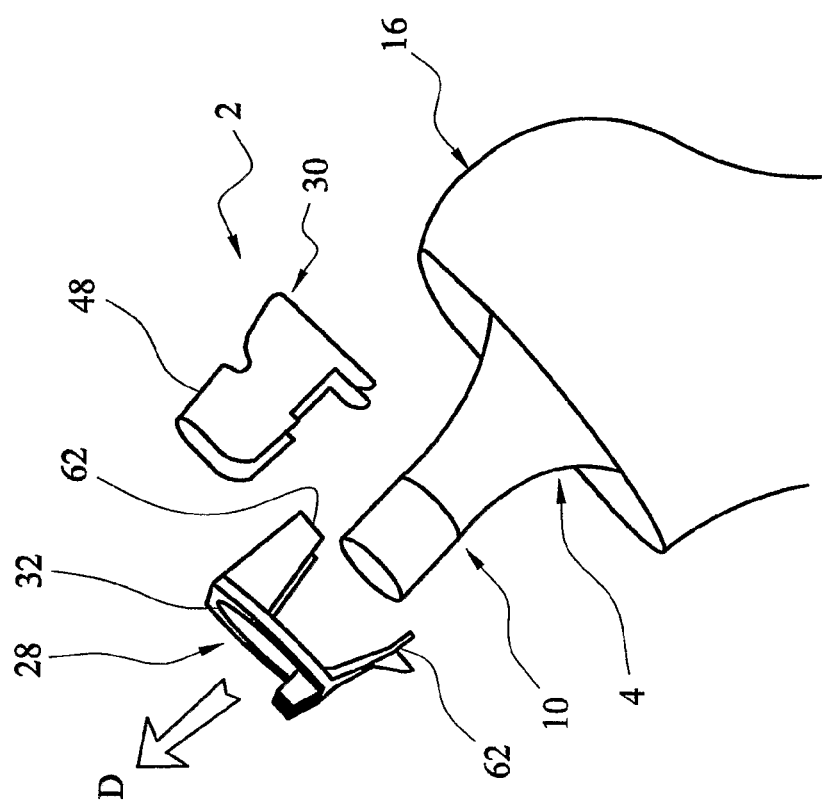
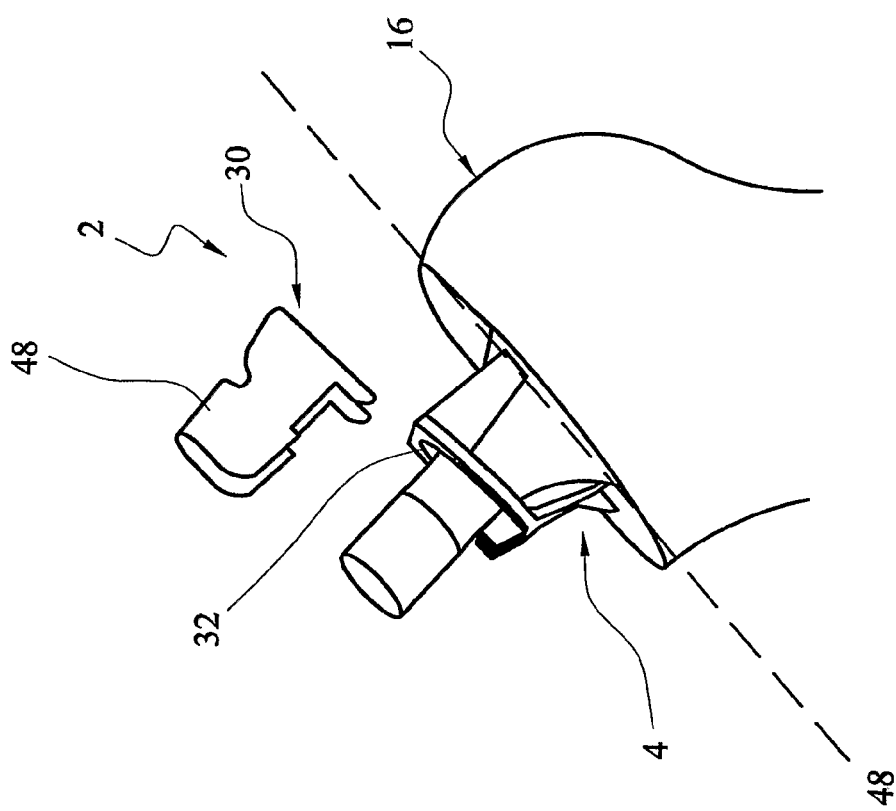
FIG. 5
FIG. 6 ably, not more than 25%, especially preferably not more
ORTHOPAEDIC JOINT PROSTHESIS IMPLANT KIT The present invention relates to an orthopaedic joint prosthesis implant kit and an implant positioning kit.

An orthopaedic joint prosthesis can be used in the repair and replacement of damaged or diseased ball-and-socket joints, and in particular are used in the repair and replacement of hip and shoulder joints. Such prostheses typically comprise a stem component which is implanted in a pre-prepared bone cavity. The stem component articulates with a mating component of the joint. For example, stem components generally have a head part which articulates with a socket component implanted in the socket of a ball-and-socket joint. The stem component can be fixed within the bone cavity by using a bone cement material.

It can be important when implanting the stem part of the orthopaedic joint prosthesis to ensure a minimum thickness of cement between the cavity wall and the stem component. If the cement mantle is too thin, then it can be sub-optimal and can lead to the stem component becoming loose within the bone cavity. This can lead to the orthopaedic joint prosthesis failing, requiring the prosthesis to be replaced.

The preferred minimum thickness of cement can vary dependent on a number of factors such as the size of the bone and implant. However, typically, for a stem component for implantation into the femur of an adult, it can be important to ensure that the cement at any point around the stem component is not less than approximately 2 mm thick and preferably the thickness of the cement is in the range of approximately 2 mm to 5 mm.

The present invention provides an implant kit which includes a positioning kit for locating a spacer between the cavity wall and the stem component at its proximal end to maintain a separation between the cavity wall and the stem component Accordingly, in one aspect, the invention provides an orthopaedic joint prosthesis implant kit comprising:
a. a stem component of an orthopaedic joint prosthesis which is intended for articulation with a mating component of the joint, having a distal end and a proximal end, and a neck part at the proximal end, the stem component being configured for fixation in a bone cavity using bone cement material with the distal end within the cavity and the proximal end at the opening of the cavity, and with the neck part protruding from the cavity towards the mating component of the joint, and
b. a positioning kit for controlling the transverse position of the stem component within the cavity at the proximal end of the stem component, comprising:
  i. at least one spacer for location between the wall of the cavity and the stem component at its proximal end to maintain a separation between the cavity wall and the stem component,
  ii. a delivery device for locating the spacer between the cavity wall and the stem component at its head end, relative to the neck part of the stem component,
in which the delivery device can be separated from the spacer so that the spacer can be retained between the cavity wall and the implanted stem component after removal of the delivery device.

The spacer can help to ensure that the distance between the implanted stem component and the cavity wall at the proximal end of the stem component at the point of the spacer, will not be less than the thickness of the spacer. The spacer can be made so that its thickness is not less than the preferred minimum thickness. Accordingly, it is an advantage of the present invention that the provision of the spacer can ensure that the cement between the implanted stem component and the cavity wall will not be less than a preferred minimum thickness, at the point of the spacer. The present invention can therefore help to ensure that the stem component is properly and securely fixed within the bone cavity.

It is also an advantage of the present invention that the spacer is located at the proximal end of the stem component. This is a significant advantage as it allows for easy implantation of the spacer. It also allows the surgeon to view the spacer to ensure that it is properly implanted.

The spacer is an article which can fit between the stem component and the cavity wall at the proximal end of the stem component. The spacer can have an annular shape so that it extends around the periphery of the proximal end of the stem component. Preferably, the spacer does not fill the entire gap extending between the cavity wall and the stem component around the periphery of the stem component at its proximal end. This is advantageous as it allows the passage of bone cement past the spacer. Preferably, the spacer extends around not more than 50% of periphery of the stem component, more preferably not more than 25%, especially preferably not more than 10%, for example not more than 5%.

There are many different preferred shapes of the spacer which include spherical, cuboidal, or arcuate. The preferred spacer shape can be an irregular shape. For example, the surface of the spacer which faces toward the stem component can be configured so that it corresponds to the contours of the stem component at its proximal end so that the spacer can fit flush against the stem component. Further, the surface of the spacer which faces toward the cavity wall can be configured so that it corresponds to the contours of the stem component so that the spacer can fit flush against the cavity wall. Preferably, the spacer is generally elongate in shape, having first and second generally planar sides. Preferably the planar sides extend generally parallel to each other. Preferably, the spacer is chamfered so that it tapers towards a point at its end distal to the delivery device. This can aid the implantation of the spacer. This is particularly the case when the bone cement has been inserted prior to implantation of the spacer. Preferably, the end of the spacer that is distal to the delivery device is rounded. This can further aid the implantation of the spacer.

The spacer need not be shaped and sized so that it contacts both, or either of the cavity wall and the stem component. In many circumstances, the spacer will not actually contact both or either of the cavity wall or the stem component, as the separation between them is greater than the thickness of the spacer. In this case, the spacer is used to ensure that the separation between the stem component and the cavity wall does not reduce over time to less than the thickness of the spacer.

Preferably, the width of the spacer, in a direction taken between the cavity wall and the proximal end of the stem component when implanted, is not more than 10 mm, more preferably not more than 5 mm, especially preferably not more than 3 mm, for example not more than 2 mm.

Preferably, the delivery device is configured to enable it to be connected temporarily to the stem component to locate the spacer relative to the neck part of the stem component. This is advantageous as it removes the need for a third party object or a surgeon to hold the delivery device during implantation of the joint prosthesis. Once the implant procedure is completed, the delivery device can be disconnected from the stem component.

Preferably, the delivery device engages the neck part of the stem component to locate the spacer relative to the neck part of the stem component. This is advantageous as it can increase the ease by which the delivery device can be connected to and disconnected from the stem component. This is because the neck part protrudes from the cavity and therefore it is generally more readily accessible to a surgeon. Also, by the delivery device engaging the neck part of the stem component, the delivery device will not interfere with the cement mixture between the cavity walls and the stem component.

Preferably, the delivery device comprises: a frame on which the spacer is carried for delivery, and a locking device which engages both the frame and the stem component to restrict relative movement between them. It can be advantageous for the delivery device to comprise at least two parts. This is because the functions of carrying the spacer and locating the spacer between the cavity wall and the stem component can be split and effected by at least two different components. This can ease of manufacture and assembly of the positioning kit. It can also increase the ease of cleaning the delivery device which can be important when the delivery device is to be used more than once. When the delivery device is configured to enable it to be connected temporarily to the stem component, then the use of two different components can also increase the ease by which the delivery device is connected to and disconnected from the neck part. The use of two different components can also be advantageous as the component which facilitates carrying of the spacer can be made from a different material from the component which facilitates location of the spacer. Accordingly, the frame can be made from a first material that is suited to the requirements of the frame, and the locking device can be made from a second material that is suited to the requirements of the locking device.

As the locking device restricts relative movement between the frame and the stem component, then the locking device can control the position of the spacer relative to the neck part of the stem component. Accordingly, the use of two different parts for a delivery device can also allow for the positioning kit to be used with multiple stem components having different sized neck parts. For example, when the positioning kit is to be used with a plurality stem components which have neck parts that differ in length, then a plurality of different sized locking devices can be provided so that an appropriate locking device can be used for a given stem component to ensure the appropriate location of the spacer relative to the stem component. Accordingly, it is possible to use the same frame for multiple stem components, as it is the locking device that controls the position of the spacer.

Preferably, the locking device engages both the frame and the neck part of the stem component to restrict relative movement between them. As discussed above, there are advantages associated with engaging the neck part of the stem component, rather than other parts of the stem component.

Preferably, the frame can be slid over the neck part of the stem component, along the axis of the neck part, in order to position the spacer between the cavity wall and the stem component at its head end. This can ease the assembly of the positioning kit. As discussed above, it is the locking device that can control the position of the spacer relative to the neck part of the stem component. Therefore, being able to slide the frame over the neck part of the stem component enables the spacers to first be located approximately in the desired position between the cavity wall and the stem component at its head end before restricting relative movement between the spacers and the stem component by the locking device.

Preferably, the locking device can be slid onto the neck part in order to engage the neck part and the frame. This can ease assembly of the delivery device. Preferably, the locking device can be slid onto the neck part, in a direction generally transverse to the axis of the neck part, in order to engage the neck part and the frame. This can ease the assembly of the delivery device, especially when the locking device engages the frame and/or the neck part of the stem component by inter-engaging formations as discussed in more detail below. This is because the inter-engaging formations can be formed so that the locking device engages the formations on the frame and/or the neck part of the stem component as the locking device is slid onto the neck part.

The locking device can engage the frame to restrict relative movement between the frame and the stem component by use of friction forces only. For example, the locking device can be a press-snap fit onto the frame. Preferably, the frame and the locking device have inter-engaging formations by which relative movement between them is restricted. This can provide for a more reliable engagement than the friction engagement. It can also be easier to assemble the delivery device when then locking device engages the frame by way of inter-engaging formations. In particular, it can be easier to disassemble the delivery device when then locking device engages the frame by way of inter-engaging.

Preferably, one of the frame and the locking device provides a rib and the other provides a hook into which the rib can be received in order to restrict relative movement between the frame and the locking device. Preferably, the hook and rib are configured so that the rib can be received in the hook as the locking device is slid onto the neck part of the stem component in a direction generally perpendicular to the axis of neck part. Preferably, the frame provides the hook and the locking device provides the rib. Preferably, the frame and the locking device provide at least two ribs and at least two hooks.

The locking device can engage the neck part to restrict relative movement between them by the use of friction forces only. For example, the locking device can be a press-snap fit onto the neck part. Preferably, the locking device and the neck part of the stem component have inter-engaging formations by which relative movement between them is restricted. This can provide for a more reliable engagement than the friction engagement. It can also be easier to assemble the delivery device when then locking device engages the neck part by way of inter-engaging formations. In particular, it can be easier to disassemble the delivery device when then locking device engages the neck part by way of inter-engaging formations.

Preferably the locking device is generally cylindrical in shape. Preferably, the side wall of the generally cylindrical locking device is open between its ends so that the locking device can be slid onto the neck part of the stem component by passing the neck part through the opening in the locking device. Preferably, the opening in the side wall of the cylindrical locking device extends at least 10% around the circumference of the cylindrical wall, more preferably at least 20%, especially preferably at least 30%, for example at least 40%. Preferably, the opening in the side wall of the cylindrical locking device extends no more than 50% around the circumference of the cylindrical wall, more preferably no more than 45%, especially preferably no more than 40%.

Preferably, the locking device restricts movement of the frame along the axis of the neck part. As the frame carries the spacer it can be important to restrict movement of the frame along the axis of the neck part so that spacer remains between the cavity wall and the stem component. It can also be important in order to prevent the spacer from moving relative to the stem component to prevent the spacers sliding into the cavity. Preferably, the locking device restricts movement of the frame along axis of the neck part away from the mating component of the joint. Preferably, the locking device restricts movement of the frame along axis of the neck part toward the mating component of the joint.

Preferably, one of the neck part of the stem component and the locking device provide a lip and the other provides a groove into which the lip can be received to restrict relative movement between the neck part and the locking device. When the locking device is a generally cylindrical in shape of which at least a part of its side wall is open, preferably, one of the lip or the groove extends around the inner surface of the cylindrical wall, and the other extends around the neck part of the stem component. Preferably, the lip and the groove extend around axes that are parallel to the axes of the neck part and the cylindrical wall of the locking device. Preferably, the lip is provided on the stem component and the groove is provided on the inner surface of the cylindrical wall.

Preferably, the proximal end of the cylindrical locking device, that will be proximal the end of the neck part most distal to distal end of the stem component is at least partially closed. Preferably, a ceiling extends across at least partway across the proximal end of the cylindrical locking device. Preferably, the ceiling extends across at least 10% of the width of the proximal end, more preferably at least 20%, especially preferably at least 30%, for example at least 40%. Preferably, the ceiling extend across not more than 90% of the width of the proximal end, more preferably not more than 80%, especially preferably not more than 70%, for example not more than 50%. The provision of the ceiling can act as a formation which can contact the proximal end of the neck part in order to restrict relative movement between them.

Preferably, the frame comprises a body part which can be slid over the neck part of the stem component, and at least one leg extending from the body part, wherein the spacer is carried on the leg. This arrangement can be advantageous as the body part can restrict transverse movement of the frame relative to the neck part of the stem component, and the leg can extend toward and into the space between the stem component and the cavity wall to carry the spacer to between the stem component and the cavity wall. Preferably, the body part is looped in configuration. Preferably, the body part is continuous, i.e. there is not a break in the looped configuration. Preferably, the body part is generally planar. The shape of the body part, when viewed along an axis extending perpendicularly to the plane of the body part, does not necessarily have to be rounded or circular in shape. For example, it can be rectangular or hexagonal in shape.

Preferably, the frame is a loose fit on neck part of the stem component. This is advantageous as it can allow the frame structure, to be used with a plurality stem components having different shapes and sizes.

It can be advantageous to allow the body part of the frame to be positioned at various points along the length of the neck part of the stem component. This is so that the position of the spacers in a direction along the axis of the neck part can be varied by varying the position of the body part. Preferably, the depth of the body part, taken in a direction perpendicular to the plane of the body part is not more than 50% of the length of the neck part of the stem component, more preferably, not more than 20% of the length of the neck part, especially preferably not more than 10% of the length of the neck part, for example not more than 5% of the length of the neck part.

Preferably, the length of the leg is not less than 5% of the length of the neck part of the neck part of the stem component, more preferably not less than 10% of the length of the neck part, especially preferably not less than 25% of the length of the neck part, especially preferably not less than 30% of the length of the neck part.

Preferably, the length extends substantially perpendicularly to the plane of the body part.

It can be advantageous to allow the transverse position of the frame relative to the neck part of the stem component to be varied. This is so that the position of the spacers in a direction perpendicular to the axis of the neck part. Preferably, the ratio of the width of width of the hole in the body part defined by the loop to the neck part, both widths being taken parallel to each other, is no less than 5:4, more preferably no less than 5:3, especially preferably no less than 2:1.

Preferably, the end of the leg distal to the body part has a foot projecting from the leg, wherein the foot can rest on the surface of the bone to restrict movement of the positioning kit relative to the bone cavity when the spacer is properly located relative to the neck part of the stem component. Normally, the bone will be resected prior to implantation of the stem component. Accordingly, in this case, the foot can rest on the resection plane of the bone. Preferably, the distal end of the foot distal to the body part is substantially planar. Preferably, the point of the foot most distal to the body part is more proximal to the body part than the spacer. This is advantageous as it can ensure that the spacer extends into the cavity, between the cavity wall and the stem component while the foot rests on the surface of the bone at cavity opening end of bone.

The leg and the spacer can be provided as one piece with a line of weakness between them which can be broken to allow the leg and the spacer to be separated. For example, the leg and the spacer can be formed as a single moulded piece wherein the line of weakness is provided by a reduction in the thickness of the moulded piece. Optionally, the leg and spacer can formed separately but and then fastened to each other by an adhesive so that they can be provided as one piece. The adhesive can act as a line of weakness. Preferably, the line of weakness can be broken by pulling the frame away from the spacer. Optionally, the line of weakness can be broken by twisting the frame relative to the spacer. Optionally, the line of weakness can be broken by cutting it with a third party object, such as a knife.

Preferably, the leg and the spacer are provided as separate pieces which are fastened to each other in such a way that allows them to be detached. Preferably, the leg and the spacer are fastened to each other by a friction fit. This can provide for a more reliable separation of the leg and the spacer. Preferably, one of the leg and the spacer include a pin projecting from it that tapers to a point, and the other comprises a corresponding tapered bore into which the pin can be received to provide a friction lock between them. Preferably the pin is provided on the leg. This can be advantageous as it can be important to reduce projections on the spacer which might interfere with surrounding tissue.

Preferably the force required to separate the frame and spacer is a force that can typically be applied by a users hand or hands or by a user using a removal tool.

It can be important to ensure that the there is a minimum thickness of cement around the entire periphery of the stem component at its proximal end. Preferably, there are provided at least two spacers for location between the wall of the cavity and the stem component at its proximal end to maintain a separation between the cavity wall and the stem component. Preferably, the delivery device is configured so that the two spacers will be located between the cavity wall and the stem component at locations which can ensure that the separation between the cavity wall and the stem component around the periphery of the stem component at its proximal end is not less than the minimum required thickness of the cement. Preferably, there are provided at least three spacers for location between the wall of the cavity and the stem component at its proximal end to maintain a separation between the cavity wall and the stem component. When there are at least three spacers provided, the delivery device can be configured so that the spacers will be located between the cavity wall and the stem component at is proximal end, so that they are spaced equally around the periphery of the stem component. The delivery device can be configured so that the spacers will be located between the cavity wall and the stem component at is proximal end, so that they are spaced equi-angularly around the periphery of the stem component.

Preferably, once the spacers have been located at the proximal end of the stem component, they are spaced around the periphery of the stem component so that they eliminate transverse movement of the proximal end of the stem component. Accordingly, if the cross-sectional shape of the proximal end of the stem component is approximately circular, then preferably three spacers are located equi-angularly around the proximal end of the stem component. The preferred location of the spacers will depend on the shape of the proximal end of the stem component. Accordingly, the skilled person would be able to adopt a technique to determine the optimum location of the spacers in order to minimise transverse movement of the proximal end of the stem component using the minimum number of spacers.

Preferably, each spacer extends around not more than 25% of periphery of the proximal end of the stem component, more preferably not more than 10%, especially preferably not more than 5%.

Providing a plurality of spacers which are located around the periphery of the proximal end of the stem component has been found to be advantageous over a single spacer. For example, once the stem component and spacers have been implanted, it has been found that an interface occurs between the cement mantle and the spacers. This interface provides a line of weakness and therefore reduces the structural integrity of the implant. Providing a plurality of spacers located around the periphery of the stem component at discrete intervals, can minimise the size of the interface between the cement mantle and the spacers.

The spacer can be made from any material which is conventionally used in the manufacture of orthopaedic prostheses. Preferred materials include curable materials, especially acrylate polymers plastics. Particularly preferred materials include polymethylmethacrylate (PMMA) or a combination of PMMA and any plastic that will not adhere to PMMA. PMMA co-polymerised with styrene can also be used. Other polymers in the PMMA series can also be used such as PEMA, PBMA, etc.

The frame can be made from any material which is conventionally used in the manufacture of orthopaedic prostheses. Preferred materials include curable materials, especially acrylate polymers plastics. Particularly preferred materials include polymethylmethacrylate (PMMA) or a combination of PMMA and any plastic that will not adhere to PMMA. PMMA co-polymerised with styrene can also be used. Other polymers in the PMMA series can also be used such as PEMA, PBMA, etc.

The locking device can be made from any material which has sufficient rigidity to restrict the movement of the locking device relative to the neck part of the stem component when external forces are exerted on the frame and locking device by the cement during implantation. For example a thermosetting or thermoplastic engineering polymer of suitable stiffness can be used, such as PET, PEI, PES, PEAK, PEEK, POM, epoxy, polyamide, polypropylene, and similar. Some of these polymers can include a filler, e.g. glass, in order to optimise or control the stiffness of the material.

A mating surface between the locking device and frame can be a soft polymer so as to increase grip and/or reduce mechanical damage. A suitable material would be a silicone based elastomer or a polyurethane based TPE.

The stem component of the orthopaedic joint prosthesis can be made from metallic based materials which are conventionally used in the manufacture of orthopaedic prostheses. Examples include certain stainless steels, alloys of titanium and certain cobalt chromium alloys.

The delivery device can include a hinge by which the delivery device can be at least partially opened. The delivery device can be a single piece and the hinge can be provided by a portion of material with mechanical properties adapted to allow the delivery device to bend about the hinge region. For example, the hinge may include a groove and or a slit to allow the delivery device to open. Alternatively, the delivery device may comprise at least two pieces which are pivotally connected by a hinge. Allowing the delivery device to be opened means that the device can be removed from the neck from the side, rather than along the neck.

The delivery device can include a grip or grips by which a user can push the delivery device open. The user can use their digit or digits to open the device, i.e. their fingers and/or thumbs. The grip or grips can be in the form of wing shaped formations. A pair of grips can be provided, one or each side of a slit in the delivery device. The pair of grips can define a generally concave structure in which a users digit or digits can be received in use.

According to a further aspect of the invention, there is provided a kit of parts for a positioning assembly for use with a stem component of an orthopaedic joint prosthesis. The kit of parts can include a collar adapted to engage about a neck of the stem component. At least one spacer separably connectable, or separably connected, to the collar can also be provided. When the spacer is attached to the collar, and with the collar engaged about the neck, the spacer can be positioned in a cavity to control the transverse separation between the stem component and the cavity.

Preferred features of the first aspect of the invention can also be preferred features of the second aspect of the invention.

Embodiments of the invention will now be described, by way of example only, and with reference to the accompanying drawings, in which:

FIG. 2 is a perspective view of the implant kit shown in FIG. 1 after a first step of the procedure of using the implant kit to implant the stem component into a bone;

FIG. 3 is a perspective view of the implant kit shown in FIG. 1 after a second step of the procedure of implanting the stem component into a bone;

FIG. 4 is a perspective view of the stem component shown in FIG. 1 after a fourth step of implanting the stem component into a bone;

FIG. 5 is a perspective view of the implant kit and the bone into which the stem component is being implanted at the fourth step in the procedure for implanting the stem component;

FIG. 6 shows a perspective view of the implant kit and bone shown in FIG. 5 after a fifth step of the procedure of implanting the stem component in the bone;

Figure 1:
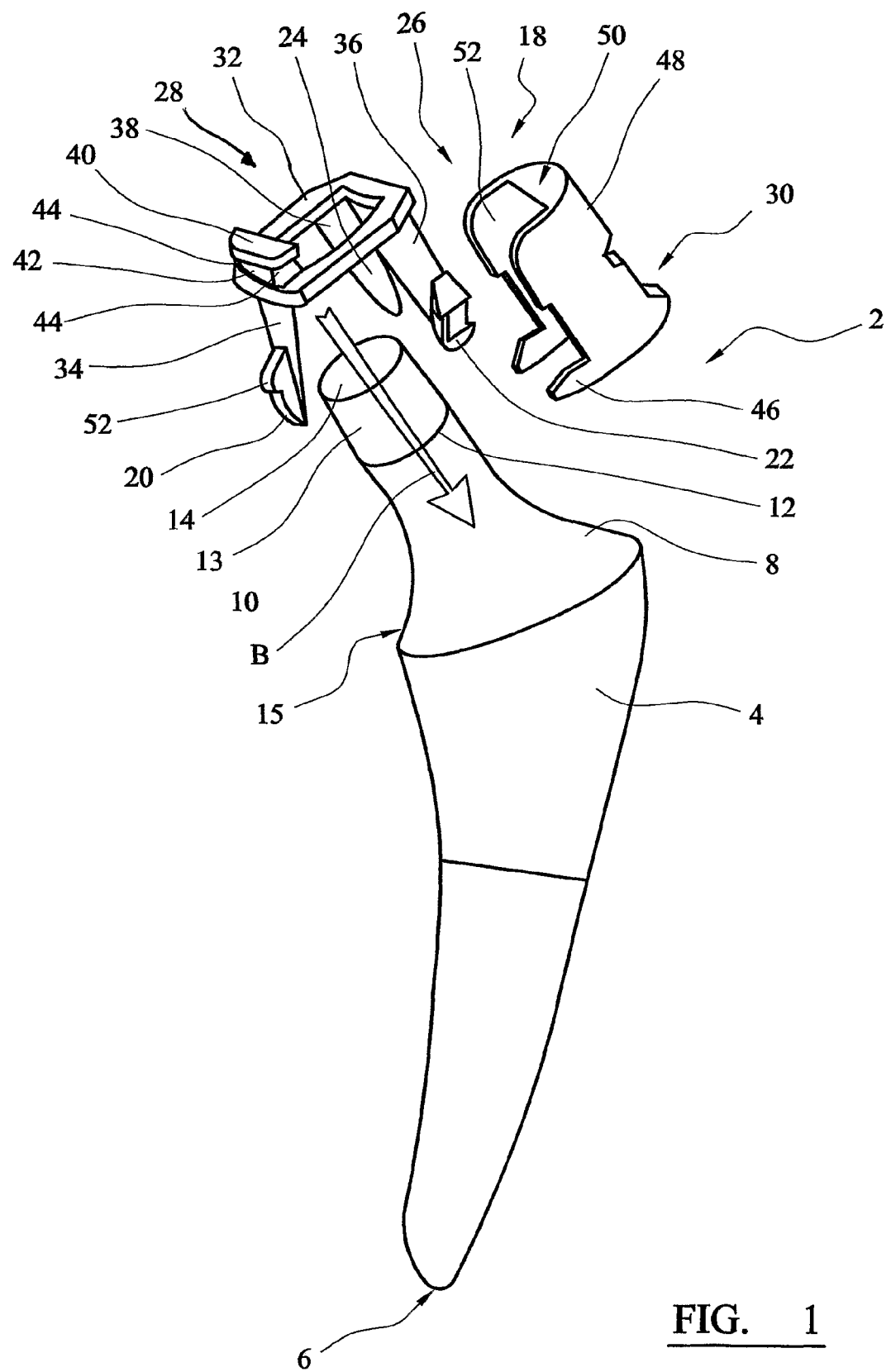
FIG. 1 is a perspective view of an orthopaedic joint prosthesis implant kit according to a first embodiment of the present invention.

Referring to the drawings, FIGS. 1 to 4 show the stem component 4 and the positioning kit 18 of the orthopaedic joint prosthesis kit 2. The stem component 4 is shown in FIGS. 5 and 6 implanted in the femur 16. The stem component 4 is shown in isolation from the femur 16 in FIGS. 1 to 4 for simplicity and ease of illustration. However, it will be appreciated that in practice, the stem component 4 shown in FIGS. 1 to 4 will be located in a pre-prepared cavity in the femur 16 during the implantation procedure.

Although the drawings show a stem component 4 suitable for inserting into a pre-prepared cavity in a femur 16, it will be appreciated that the invention can be applied to other orthopaedic joint prostheses, for example, a shoulder joint prosthesis.

The stem component 4 has a distal end 6 which is located in the femur in use and a proximal end 8, the majority of which extends from the resected surface of the femur. The proximal end 8 has a shoulder part 15 which extends into a neck part 10 which has a connector for attaching to a head component in the form of a generally tapering formation, referred to herein as the taper 13. In use, the neck part 10 and taper 13 protrudes from the cavity within the femur 16. The junction between the neck part 10 and taper 13 has a lip 12 extending around the periphery approximately a third of the way along the length of the exposed part of the stem component from the top end 14 of taper 13 to the shoulder portion 15. The top end 14 of the taper 13 is generally planar and is rounded in shape, particularly circular in shape, when viewed along the longitudinal axis of the neck part 10. The taper connector 13 between the lip 12 and its top end 14 tapers inwardly from the lip 12 to the top part 14. The taper 13 part of the neck part 10 provides a connector for receiving a head part (not shown) of the joint prosthesis which has a generally part-spherical shape and which can articulate in a mating pelvic component of the joint prosthesis.

The positioning kit 18 comprises three spacers 20, 22, 24 and a delivery device 26 comprising a frame 28 and a locking device 30.

The frame 28 comprises a generally annular planar body part 32 having four elongate generally straight side members. The side members are joined at their ends to form a looped configuration so that the body part can fit over the neck part 10 of the stem component 4 like a collar as shown in FIGS. 2 to 5. The frame 28 further comprises three legs 34, 36, 38 extending downwardly from the body part 32.

Each leg extends from the body part at the first ends of the legs, in a direction generally perpendicular to the plane of the body part 32. Each leg 34, 36, 38 carries at its second end distal to the body part, a spacer 20, 22, 24. Each leg 34, 36, 38 is spaced approximately equally around the body part 32. A first medial leg 34 supports spacer 20 at adjacent a medial part of the stem, a second anterior leg 36 supports spacer 22 adjacent an anterior part of the stem and a third posterior leg 38 supports spacer 24 adjacent a posterior part of the stem. This is the case for a left hand stem and for a right hand stem the anterior and posterior legs will swap. The legs locate the spacers around the should of the stem in the vicinity of the resection plane 60 of the femur as illustrated in FIG. 3.

There is further provided a bar 40 on one of the side members of the body part 32. The bar 40 extends substantially perpendicular to the plane of the body part 32 and is spaced from the body part by a post 42 which extends between the bar 40 and the side member of the body part 32. The dimensions of the bar 40, the post 42 and the end member of the body part 32 are such that the bar and the end member of the body part 32 define a space at each end of the bar. Accordingly, the bar 40, the post 42 and the end member of the body part 32 define a hook shaped formation 44 at each end of the bar, the hooks being suitable for receiving protrusions 46 of the locking device 30.

The spacers 20, 22, 24 have a rounded end portion and a tapered portion at their opposite end which is proximal to the leg on which it is fastened. Each spacer 20, 22, 24 has a chamfered surface at its rounded end.

Each leg has a pin 62 extending from its second end which can each be received within respective correspondingly shaped holes (not shown) in each spacer in order for the spacers to be releasably fastened to the legs by a friction fit.

The frame 32 further comprises a foot 52, 54 at the distal end of each leg 34, 36, 38. The feet protrude from the legs generally perpendicularly to the longitudinal axes of the legs. The feet have generally planar engaging surfaces that extend away from the body part 32 to abut with the surface of the resected femur in use.

The locking device 30 comprises a generally cylindrical body 48 wherein at least a part of its side wall is open between its ends so that the locking device 30 can be slid on to the taper 13 in a direction generally transverse to the longitudinal axis of the neck part as illustrated by arrow A in FIG. 2. The locking device 30 is open at both of its ends. However the proximal end of the delivery device which will be adjacent the proximal end of the taper 13 of the stem component 4 when in use, includes a ceiling 50 which extends part way across the open end of the generally cylindrical body 48.

The delivery device further comprises a recess 52 extending around the inner periphery of the cylindrical body 48 approximately half way along its length between the ends of the body 48. The body 48 and the recess 52 are configured so that when the locking device 30 is slid on to the taper 13, a lower edge of the recess 52 engages the lip 12 on the taper 13 and the ceiling 50 fits flush with the top part 14 of the taper 13 so that there is no space between them and to provide a snug, push fit fastening between the locking device 30 and the taper 13. The locking device 30 further comprises protrusions or feet 46 extending from its distal end which can engage with the hooks provided by the bar 40 and the body part 32 of the frame 28 so as to fix the position of the frame relative to the stem, and in particular with reference to the taper 13.

In use, the frame 28 is slid over the neck part 10 along the access of the neck part like a collar in a direction indicated by arrow B until the frame cannot be slid along the axis any further as shown in FIG. 2. The spacers 20, 22, 24 will then be approximately in their desired position in the vicinity of the resection plane of the femur and located between the stem component 4 and the inner wall of the cavity in the femur 16.

The locking device 30 is then slid on to the taper 13 in a direction generally transverse to the axis of the neck part as illustrated by arrow A in FIG. 2. The locking device 30 is slid on to the taper 13 until the protrusions 46 extended into the hooks provided by the bar 40, the post 42 and the body part 32 of the frame 28. At this stage, the ceiling 50 of the locking device 30 abuts the planar top end 14 of the taper 13 and the ridge 52 engages the lip 12 of the taper 13. Accordingly, the ceiling 50 and the ridge 52 prevent movement of the locking device 30 in a direction parallel to the axis of the neck portion 10. Further, because the protrusions 46 of the delivery device 30 extend into the hooks provided by the body part 32 of the frame 28 and the bar 40, the frame 28 is prevented from moving in a direction parallel to the axis of the neck part 10.

Accordingly, the delivery device 30 controls the location of the spacers 20, 22 and 24. When assembled correctly, the spacers 20, 22, 24 will be located between the inner wall of the cavity in the bone 16 and the stem component at its proximal end in order to maintain a separation between the inner wall of the cavity and the outer surface of the stem component. The spacers 20, 22, 24 are located so that their end proximal to the legs will be positioned at the resection plane 60 of the bone 16. The feet 52, 54 on the legs abut the resected surface of the femur and control the depth of insertion of the stem component into the cavity to prevent the stem component from being inserted too far into the femur.

Once the spacers 20, 22, 24 have been properly positioned, then the gap between the cavity wall of the femur 16 and the stem component 4 is filled with a bone cement. Alternatively, or additionally, the cavity can be filled with bone cement before the positioning kit is used to position the spacers 20, 22, 24 between the cavity wall and the stem component 4.

The delivery device 26 is then removed from the stem component as illustrated in FIGS. 4 to 6. Firstly, the locking device 30 is slid off the taper 13 in a direction generally transverse to the axis of the neck part 10 in the direction illustrated by arrow C in FIG. 4. Once the locking device 30 is free from the hooks provided by the bar 40 and the body part 32 of the frame 28, the frame can be removed from the stem component by sliding it off the neck part 10 of the stem component in a direction generally parallel to the axis of the stem component as illustrated by arrow D in FIG. 6. The stiction forces between the spacers 20, 22, 24 and the bone cement ensures that the spacers detach from the delivery device and remain between the cavity wall and the stem component when the frame 28 is slid along the axis of the neck portion 10 to retain the stem in the correct position within the cavity.

Hence, by using spacers, the stem component can be correctly positioned to ensure that there is sufficient separation between the inner wall of the cavity and the outer surface of the stem so that a sufficient thickness of bone cement is provided around the stem. Further, the delivery device delivers the spacers to the correct position relative to the stem component. The delivery device also ensures that the stem component is inserted to the correct depth in the femoral cavity.

Figure 7:
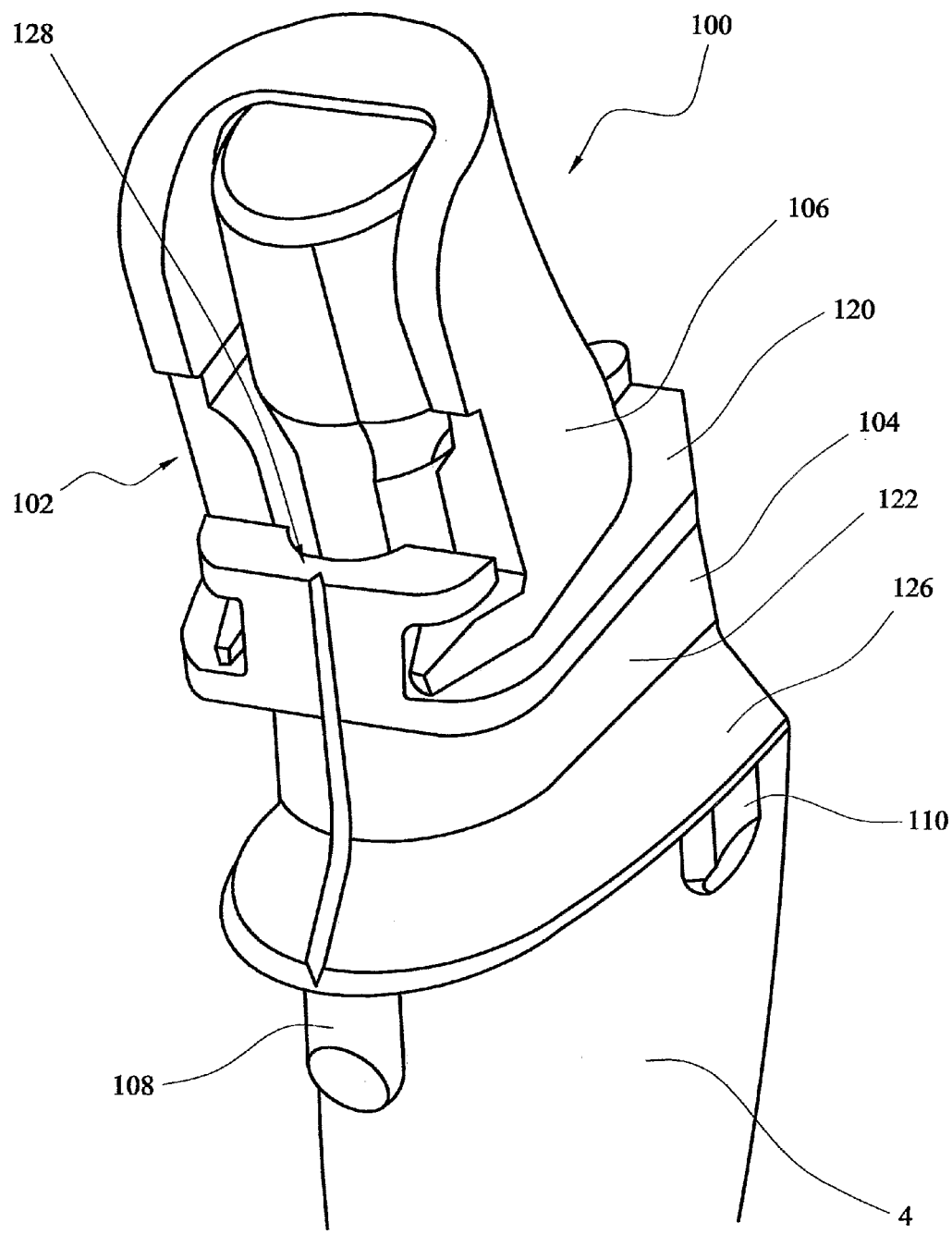
FIG. 7 shows a front perspective view of a second embodiment of the invention.
Figure 8:
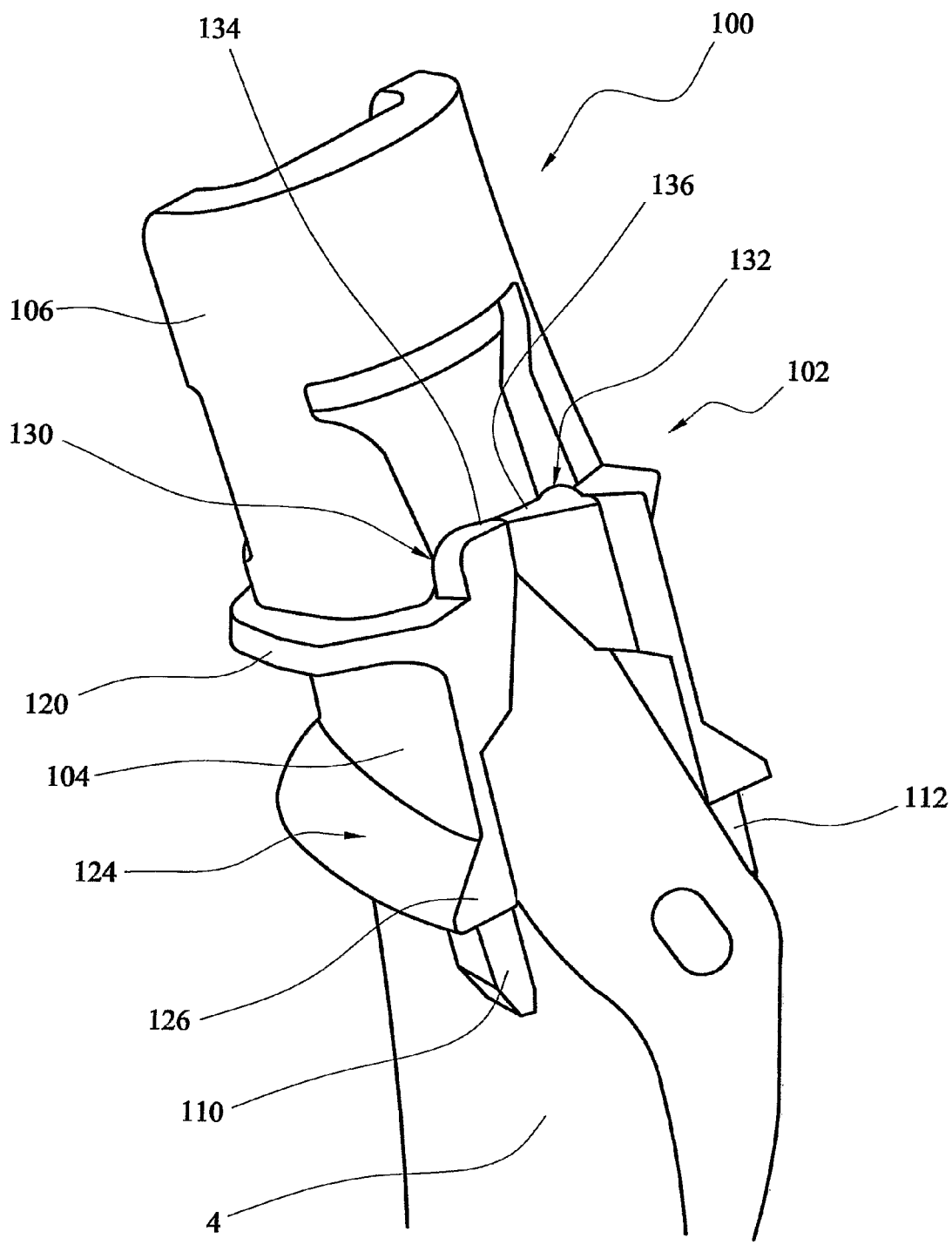
FIG. 8 shows a rear perspective view of the second embodiment shown in FIG. 7.
Figure 9:
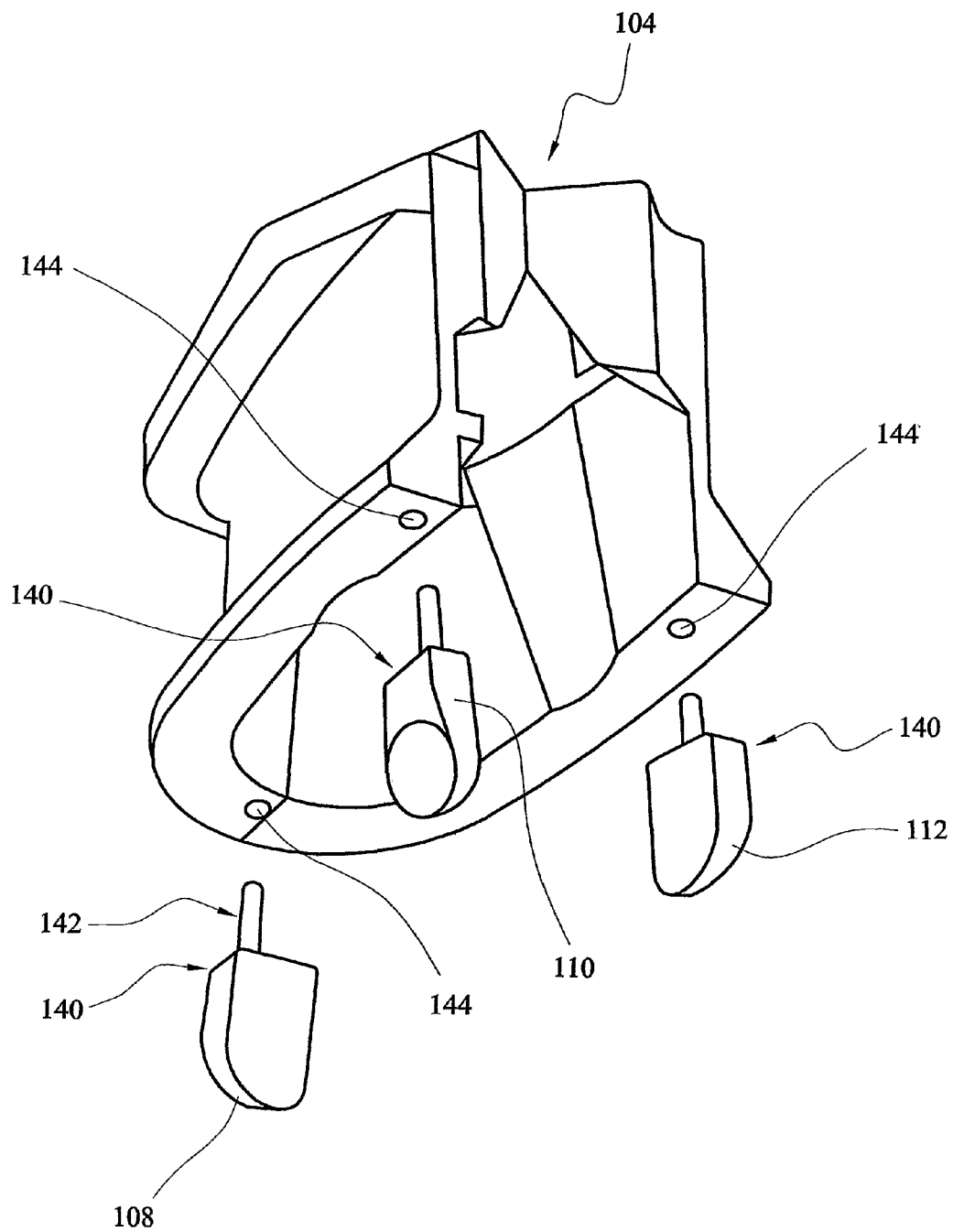
FIG. 9 shows an exploded perspective view of a delivery part and spacer parts of the embodiment shown in FIGS. 7 and 8.

FIGS. 7 to 9 show a further embodiment of the positioning kit 100 according to the present invention. Positioning kit 100 includes a two part delivery device 102 including a collar 104 and a locking device 106 and also three detachable spacers 108, 110, 112. Locking device 106, collar 104 and spacers 108, 110, 112 are similar to locking device 30, frame 28 and spacers 20, 22, 24 respectively. The substantial differences will be described below.

Collar 104 is in the form of a generally solid body rather than being in the form of a frame. Collar 104 has an upper annular body 120 from which a skirt 122 downwardly depends and extends around substantially the front and side portions of the collar. Free end 124 of skirt 122 flares outwardly and increases in thickness to provide a single foot 126 that extends continuously around the lower extremity of the collar and about the front and side portions of the collar. Foot 126 provides a formation for abutting against the resected surface of the femur in use to control the depth of insertion of the implant similarly to the three separate feet of the first embodiment.

A front part of the collar includes a region of weakened mechanical strength, or a break or fracture line, 128 which allows the collar either to be opened up or split in half for removal as will be described in greater detail below. The weakened region 128 is provided by a V-shaped groove on the outer surface and a corresponding slit on the inner surface so that the thickness of material is reduce to provide a live hinge by which the collar can be pulled open. For example, the thickness of material can be approximately 0.3 mm between the groove and inner slit.

Toward the rear of the collar there are provided two grip formations each on a respective side of a narrow split in the collar. The grips are generally in the form of wings defining a generally concave structure for receiving a users thumbs to pull the collar open and apart. Above the grip formations 130, 132 are two respective projections 134, 136 which extend upwardly from an upper surface of the annular body 120 of the collar. Locking device 30 has an aperture in a lower part which has substantially the same width as the projections 134, 136. Hence, when assembled in use, as illustrated in FIG. 8, the projections are retained or captured in the aperture in the locking device to prevent the collar from opening. When the locking device has been removed, the collar can be easily removed by the user urging the collar apart with their thumbs on the grips 134, 136 so that the collar opens about the front groove. In different embodiments, the collar may simply break into two separate pieces by suitably configuring the materials properties.

The spacers 108, 110, and 112 differ to those described above in a number of ways. Each spacer 108, 110, 112 is identical and so only a single spacer needs to be manufactured. The top front edge 140 of each spacer is bevelled to allow the spacer to take up the correct angular position when attached to the medial position on the collar owing to the medial curvature of the stem. Three holes 144 are provided in the foot 126 to accept a press fit peg part 142 of the spacer. The peg part is off set to one side of the middle of the spacer body so that with suitably positioned holes 144, the same spacer can be used in any of the three positions, anterior, posterior or medial. As illustrated in FIG. 9, the medial hole is positioned to one side of the break line 128, and the anterior hole is located closer to the rear of the collar than the posterior hole (or vice versa depending on whether the collar is for a left or right stem). Hence, as the peg is off set, the same spacer can be used for each hole position.

The positioning kit is used similarly to the first embodiment, except that to remove the collar, after the locking device has been removed, the collar is urged apart to remove the collar rather than sliding the collar up the neck of the stem. The spacers are left in the cement in the stem/cavity gap as they disengage from the collar.

Although the spacers have been described as being push fit, any other mechanism for separably connecting the spacers to the collar or frame can be used. For example, the spacers can be attached by a frangible connection, such as a region of material of weak strength, specially designed to break when the collar or frame is removed, leaving the spacers in the cement. An adhesive which is sufficient to attach the spacers to the collar or frame but which is not strong enough to overcome the stiction of the cement can also be used. Other types of releasable mechanical fastenings can also be used, such as various push fit, press fit or friction fit type mechanisms.

The invention claimed is:

1. An orthopaedic joint prosthesis implant kit comprising:
   a stem component of an orthopaedic joint prosthesis intended for articulation with a mating component of the joint, having a distal end and a proximal end, and a neck part at the proximal end, the stem component being configured for fixation in a bone cavity using bone cement material with the distal end within the cavity and the proximal end at the opening of the cavity, and with the neck part protruding from the cavity towards the mating component of the joint; and a positioning kit for controlling the transverse position of the stem component within the cavity at the proximal end of the component, comprising:
  i. at least two spacers for location between the wall of the cavity and the stem component at its proximal end to maintain a separation between the cavity wall and the stem component, wherein, when located between the stem component and the cavity wall, each of the spacers extends around not more than 10% of the periphery of the stem component; and
  ii. a delivery device attached to the at least two spacers for locating the spacers between the cavity wall and the proximal end of the stem component relative to the neck part of the stem component.

2. The implant kit of claim 1, wherein the delivery device is configured to be connected temporarily to the stem component to locate the at least two spacers relative to the neck part of the stem component.

3. The implant kit of claim 2, wherein the delivery device is configured to engage the neck part of the stem component to locate the at least two spacers relative to the neck part of the stem component.

4. The implant kit of claim 1, wherein the delivery device comprises a frame on which the at least two spacers are carried for delivery, and a locking device that engages the frame and the stem component to restrict relative movement therebetween.

5. The implant kit of claim 4, wherein the locking device engages the frame and the neck of the stem component to restrict relative movement therebetween.

6. The implant kit of claim 5, wherein the locking device slidably engages the neck in a direction generally transverse to the neck axis.

7. The implant kit of claim 5, wherein the frame and the locking device have inter-engaging formations by which relative movement therebetween is restricted.

8. The implant kit of claim 5, wherein the locking device and the neck of the stem component have inter-engaging formations by which relative movement therebetween is restricted.

9. The implant kit of claim 5, wherein the locking device restricts movement of the frame along the neck axis away from the mating component of the joint.

10. The implant kit of claim 5, wherein the locking device restricts movement of the frame along the neck axis towards the mating component of the joint.

11. The implant kit of claim 4, wherein the neck has a neck axis and the frame slidably engages the neck of the stem component along the neck axis.

12. The implant kit of claim 4, wherein the frame comprises a body that is slidable over the neck of the stem component, and at least one leg extending from the body part, wherein one of the at least two spacers is carried on the leg.

13. The implant kit of claim 12, wherein the end of the leg distal to the body part has a foot projecting from the leg, wherein the foot can rest on the surface of the bone to restrict movement of the body part relative to the bone cavity when the one of the at least two spacers is located relative to the neck part of the stem component.

14. The implant kit of claim 12, wherein the leg and the one of the at least two spacers are provided as one piece with a line of weakness therebetween that can be broken to allow the leg and said spacer to be separated.

15. The implant kit of claim 12, wherein the leg and said spacer are provided as separate pieces that are detachably attached to one another.

16. The implant kit of claim 15, wherein the leg and said spacer are fastened to one another by a friction fit.

17. The implant kit of claim 1, wherein said spacer tapers towards a point at its end distal to the delivery device.

18. A kit of parts for a positioning assembly for use with a stem component of an orthopaedic joint prosthesis having a distal end and a proximal end, and a neck at the proximal end, the stem component being configured for fixation in a bone cavity using bone cement material with the distal end within the cavity and the proximal end at the opening of the cavity, and with the neck protruding from the cavity, the kit of parts comprising:
  a delivery device including a collar adapted to engage about the neck; and
  at least two spacers separably connectable or separably connected to the collar, wherein when the spacers are attached to the collar, and with the collar engaged about the neck, the spacers are positioned in the cavity to control the separation between the stem component and the cavity, and wherein, when located between the stem component and the cavity wall, each of the spacers extends around not more than 10% of the periphery of the stem component.

19. The kit of claim 18, wherein the stem has a longitudinal axis and the delivery device includes a hinge by which the delivery device can be at least partially opened to allow the delivery device to be removed at least partially transversely to the longitudinal axis.

20. The kit of claim 19, wherein the delivery device includes grips by which a user can open the delivery device using their digits.

* * * * *